United States Patent
Redwine

(12) 
(10) Patent No.: US 8,030,531 B2
(45) Date of Patent: *Oct. 4, 2011

(54) PROCESS FOR PRODUCTION OF 2,3-DICHLOROBUTADIENE-1,3

(75) Inventor: Terry Wayne Redwine, Ponchatoula, LA (US)

(73) Assignee: Dupont Performance Elastomers LLC, Wilmington, DE (US)

( * ) Notice: Subject to any disclaimer, the term of this patent is extended or adjusted under 35 U.S.C. 154(b) by 415 days.

This patent is subject to a terminal disclaimer.

(21) Appl. No.: 12/335,598

(22) Filed: Dec. 16, 2008

(65) Prior Publication Data

US 2009/0163745 A1 Jun. 25, 2009

Related U.S. Application Data

(60) Provisional application No. 61/008,160, filed on Dec. 19, 2007.

(51) Int. Cl.
*C07C 23/00* (2006.01)

(52) U.S. Cl. ........ 570/246; 570/189; 570/216; 570/226; 570/227

(58) Field of Classification Search ........................ None
See application file for complete search history.

(56) References Cited

U.S. PATENT DOCUMENTS

| 2,626,964 | A | * | 1/1953 | Eberly et al. | 570/229 |
|---|---|---|---|---|---|
| 3,639,493 | A | | 2/1972 | Campbell | |
| 3,876,716 | A | | 4/1975 | Campbell | |
| 3,981,937 | A | * | 9/1976 | Campbell et al. | 570/228 |
| 4,104,316 | A | | 8/1978 | Scharfe et al. | |
| 4,215,078 | A | | 7/1980 | Hargreaves, II et al. | |
| 4,629,816 | A | * | 12/1986 | Heinrich et al. | 570/229 |
| 6,380,446 | B1 | | 4/2002 | Drew et al. | |

OTHER PUBLICATIONS

U.S. Appl. No. 12/335,583, filed Dec. 16, 2008, Terry Wayne Redwine.

* cited by examiner

*Primary Examiner* — Sudhakar Katakam

(57) ABSTRACT

2,3-dichlorobutadiene-1,3 of high purity is produced from 1,2,3,4-tetrachlorobutane by a process comprising the steps of dehydrochlorination, chlorination of the reaction product obtained in the dehydrochlorination step and subsequent separation of a 2,3-dichlorobutadiene-1,3 composition from the reaction product of the chlorination step.

6 Claims, No Drawings

US 8,030,531 B2

PROCESS FOR PRODUCTION OF 2,3-DICHLOROBUTADIENE-1,3

CROSS-REFERENCE TO RELATED APPLICATIONS

This application claims the benefit of U.S. Provisional Application No. 61/008,160, filed Dec. 19, 2007.

FIELD OF THE INVENTION

The present invention is directed to an improved process for production of 2,3-dichlorobutadiene-1,3 from 1,2,3,4-tetrachlorobutane.

BACKGROUND OF THE INVENTION

Polychloroprene is a commercially useful elastomeric polymer of 2-chlorobutadiene-1,3 ("chloroprene") that has found utility for over seventy years in manufacture of rubber belts, hoses, engine mounts, adhesives and rubber profiles. The polymer may be a homopolymer, i.e. a polymer that is made up solely of copolymerized units of chloroprene monomer, or it may be a copolymer that contains copolymerized units of chloroprene and other comonomers. Because of the extremely high reactivity of chloroprene, it tends to homopolymerize. The amount of comonomer that can be introduced into the polymer chain by copolymerization is generally only about 2 mole percent in the case of tetrachlorobutadiene and even less for styrene and isoprene when overall monomer conversion is 65% and the initial level of comonomer present is 10 mole %. 2,3-dichlorobutadiene-1,3 is one of the few monomers that is more reactive than chloroprene itself. This characteristic has facilitated its use as a comonomer in the manufacture of a variety of polychloroprene copolymers, most of which have outstanding crystallization resistance and low temperature properties.

Synthesis of 2,3-dichlorobutadiene-1,3 may be accomplished by a number of methods that generally involve a dehydrochlorination reaction as a process step. For example, U.S. Pat. No. 4,215,078 describes a process for dehydrochlorination wherein the reaction is carried out with an aqueous mixture of sodium hydroxide and sodium chloride having the composition of a chlor/alkali cell liquor. U.S. Pat. No. 4,629,816 discloses a process for dehydrochlorination of 2,3,4-trichlorobutene-1 carried out under conditions where an alkali metal hydroxide solution is added to a mixture of the 2,3,4-trichlorobutene-1, phase transfer catalyst, inhibitor and water, while U.S. Pat. No. 6,380,446 describes the use of an upflow reactor in the dehydrohalogenation of various halogenated alkane and alkene compounds, including chlorinated butenes.

These dehydrohalogenation processes are typically conducted in the liquid phase by mixing the halogenated alkane or halogenated alkene with a strong base in a solvent. Because the base is usually added as an aqueous solution, phase transfer agents (also referred to as phase transfer catalysts) are usually employed to promote contact of the reactants. These catalytic materials promote reaction between reactants located in different phases by transferring one reactant across the interface into the other phase so that the reaction can proceed. The phase transfer agent is not consumed and performs the transport function repeatedly. See, e.g. Starks et al, "Phase-Transfer Catalysis", Academic Press, New York, N.Y. 1978.

Although phase transfer catalysts are very effective at increasing conversion in some dehydrochlorination reactions, these higher conversions can result in increased formation of byproduct isomers that are difficult or impossible to remove from the desired product. In the dehydrochlorination of 3,4-dichlorobutene-1 to produce chloroprene for example, the reaction of some impurities in the organic reactant forms byproduct chlorobutadienes that contain chlorine substituents located at an alpha carbon (i.e. "alpha-chlorine"). As used herein, the term "alpha carbon atom" means a carbon at the end of a carbon chain (either an alkyl or alkenyl chain) generally numbered 1 in the IUPAC naming convention for alkanes and alkenes. By extension, a beta carbon atom is a carbon atom at the penultimate end of a carbon chain ("next to last" or second) generally numbered 2 in the IUPAC naming convention for alkanes and alkenes.

One method of controlling the problem of byproduct formation in dehydrochlorination reactions is by intentionally limiting reactant conversion to a level below that which is otherwise achievable. However, although intentionally limiting reactant conversion allows acceptable product purity to be attained, it also reduces yield and imposes an economic and environmental disadvantage that can be significant. In another example, high conversion conditions in the dehydrochlorination of 1,2,3,4-tetrachlorobutane to form 2,3-dichlorobutadiene-1,3 results in production of substantial amounts of isomeric dichlorobutadienes that contain alpha-chlorine substituents (i.e. chlorine atoms attached to alpha carbon atoms). The presence of isomeric products that contain alpha-chlorine substituents is objectionable because use of such mixtures as monomer feeds in polymerization reactions of 2,3-dichlorobutadiene-1,3, including copolymerization reactions with chloroprene, can result in formation of relatively high percentages of allylic chlorine in the polymer backbone. This can increase oxidative degradation of the polymer.

Removal of isomers containing alpha-chlorine substituents from desired products such as 2,3-dichlorobutadiene-1,3 that contain chlorine exclusively at beta carbons is difficult because the isomers generally have similar volatilities. Attempts made in the past to address this problem have not been completely satisfactory. For example, in U.S. Pat. No. 2,626,964 a method is described for increasing the purity of 2,3-dichlorobutadiene-1,3 formed via dehydrochlorination of 1,2,3,4-tetrachlorobutane by repressing the dehydrochlorination of 1,2,4-trichloro-2-butene formed in the reaction. Although the purity is increased somewhat, low overall yield and long reaction times detract from the commercial usefulness of this method.

Because of the difficulties associated with separation of isomers, conversion in dehydrochlorination reactions is typically intentionally limited to levels lower than those that are readily achievable in order to reduce formation of isomers containing alpha-chlorine substituents to acceptable levels.

It would be advantageous to have a method available that would permit attainment of high conversion in dehydrochlorination of 1,2,3,4-tetrachlorobutane as well as in the dehydrochlorination of compounds that can be used as intermediates in the formation of 2,3-dichlorobutadiene-1,3 while at the same time provide acceptable product purity.

SUMMARY OF THE INVENTION

The present invention is directed to a process for production of a 2,3-dichlorobutadiene-1,3 composition, the process comprising the steps of:

A. contacting a composition comprising 1,2,3,4-tetrachlorobutane with an aqueous mixture comprising a base having a $K_b$ of at least $10^{-9}$, at a temperature sufficient to dehydrochlorinate said 1,2,3,4-tetrachlorobutane, thereby forming a first reaction product having at least two phases, 1) a first phase comprising a mixture of a) 2,3-dichlorobutadiene-1,3 and b) a chlorinated byproduct comprising chlorinated butenes other than 2,3-dichlorobutadiene-1,3 and 2) a second phase comprising an aqueous phase;

B. separating said first phase from said aqueous phase;

C. contacting said first phase, after it has been separated from said aqueous phase, with chlorine having a purity of at least 96% in an amount sufficient to further chlorinate said chlorinated byproduct but insufficient to cause conversion of more than 20% of the 2,3-dichlorobutadiene-1,3 that is present in said first phase to more highly chlorinated species, thereby producing a second reaction product; and D. isolating from said second reaction product a composition comprising 2,3-dichlorobutadiene-1,3 wherein at least 90 weight percent of said composition is 2,3-dichlorobutadiene-1,3, based on the total weight of said composition.

The invention is further directed to a composition comprising 2,3-dichlorobutadiene-1,3, prepared by a process comprising the steps of:

A. contacting a composition comprising 1,2,3,4-tetrachlorobutane with an aqueous mixture comprising a base having a $K_b$ of at least $10^{-9}$, at a temperature sufficient to dehydrochlorinate said 1,2,3,4-tetrachlorobutane, thereby forming a first reaction product having at least two phases, 1) a first phase comprising a mixture of a) 2,3-dichlorobutadiene-1,3 and b) a chlorinated byproduct comprising chlorinated butenes other than 2,3-dichlorobutadiene-1,3 and 2) a second phase comprising an aqueous phase;

B. contacting said first phase with chlorine having a purity of at least 96% in an amount sufficient to further chlorinate said chlorinated byproduct but insufficient to cause conversion of more than 20% of the 2,3-dichlorobutadiene-1,3 that is present in said first phase to more highly chlorinated species, thereby producing a second reaction product; and C. isolating from said second reaction product a composition comprising 2,3-dichlorobutadiene-1,3 wherein at least 90 weight percent of said composition is 2,3-dichlorobutadiene-1,3, based on the total weight of said composition.

DETAILED DESCRIPTION OF THE INVENTION

The process of the present invention is generally applicable to the production and isolation of 2,3-dichlorobutadiene-1,3 from 1,2,3,4-tetrachlorobutanes, including meso-1,2,3,4-tetrachlorobutane.

The process of the invention involves a first dehydrochlorination step to produce a mixture of the desired 2,3-dichlorobutadiene-1,3 along with a byproduct composition that will generally contain a number of chlorinated alkane and chlorinated alkene species different from the desired chlorinated butadiene. The mixture is then contacted with gaseous chlorine, preferably of purity above 96%, under conditions that are sufficient to further chlorinate some or all of the chlorinated alkane and/or chlorinated alkene species in the byproduct composition, the conditions being insufficient to cause conversion of more than 20% of the 2,3-dichlorobutadiene-1,3 to more highly chlorinated species. By gaseous chlorine of 96 wt. % purity is meant a gaseous chlorine composition that contains at least 96 wt % chlorine, the remainder being other gaseous components, such as carbon dioxide, nitrogen and hydrogen chloride. The product of the chlorination reaction is a material that lends itself to facile separation of the desired 2,3-dichlorobutadiene-1,3 from most of the undesired chlorinated byproducts.

The 1,2,3,4-tetrachlorobutane composition that serves as the reactant in the dehydrochlorination step of the process comprises any isomer of 1,2,3,4-tetrachlorobutane, including meso-1,2,3,4-tetrachlorobutane, which is preferred. The 1,2,3,4-tetrachlorobutane may comprise a pure isomer or it may be a mixture of isomers. The 1,2,3,4-tetrachlorobutane may also comprise species other than 1,2,3,4-tetrachlorobutane, for example mixtures with chlorinated butenes. For example, a mixture of chlorinated alkanes and alkenes from a prior process step or from a prior reaction step in the same vessel may be dehydrochlorinated or undergo a subsequent dehydrochlorination reaction according to the process of the present invention. In such cases, the byproduct composition will generally contain isomers of chlorinated butanes or chlorinated butenes.

The dehydrohalogenating agent that is suitable for use in the process of the invention is a base having a $K_b$ of at least $10^{-9}$. The base will generally be in the form of an aqueous solution, but it need not be. Suitable bases include pyridine, trimethylamine, ammonia, ammonium hydroxide, calcium hydroxide, alkali metal hydroxides, and alkali metal alkoxides. Preferably the base will have a $K_b$ of at least $10^{-5}$, and most preferably the base will be completely ionized, as in the case of aqueous alkali. Any aqueous alkali metal hydroxide is suitable for purposes of the invention, but sodium hydroxide and potassium hydroxide are preferred. The alkali normally will be present in excess in the reaction mixture. Generally, a mole ratio of alkali to halogenated reactant will be approximately 1.01-2.50. The precise amount will be determined based on factors such as the type of catalyst used and the particular reactants.

According to the process of the invention, the dehydrohalogenation reaction takes place in the liquid phase at a temperature sufficient to dehydrochlorinate 1,2,3,4-tetrachlorobutane. The reaction mixture will normally contain at least one liquid. For example, the halogenated reactants may be liquids under conditions of the reaction or they may be dissolved in aqueous or non-aqueous solvents. If the reactants are present as solutions, the solvents may be miscible or immiscible. In a preferred embodiment the halogenated reactant is in liquid form and an alkali metal hydroxide dehydrohalogenating agent is present as an aqueous solution. In addition, the dehydrohalogenation may take place in the presence of a non-aqueous solvent such as methanol, for example as disclosed in U.S. Pat. No. 4,104,316.

A phase transfer catalyst is preferably used to promote contact between the two immiscible liquids, i.e. the organic and aqueous phases, thereby promoting the dehydrochlorination reaction. However, the process of the invention may also be conducted in the absence of a phase transfer catalyst. Preferred catalysts are quaternary ammonium salts, especially quaternary ammonium chlorides, particularly those represented by the formula $R^1R^2R^3R^4NCl$ in which each of $R^1$, $R^2$ and $R^3$ independently is a $C_1$-$C_{20}$ alkyl, a $C_2$-$C_{20}$ alkenyl, or a $C_7$-$C_{20}$ aralkyl, and $R_4$ is a $C_6$-$C_{20}$ alkyl or alkenyl, benzyl, or a ($C_6$-$C_{20}$) alkyl- or alkenyl-substituted benzyl. Each of the $R^1$, $R^2$, and $R^3$ groups in these quaternary ammonium chlorides may also contain a hydroxyl or ether group in a position beta to the nitrogen atom. The amount of the quaternary ammonium compound is generally about 0.01-10% by weight of the starting halogenated alkane or alkene. Other phase transfer catalysts include amine oxides, such as those disclosed in U.S. Pat. No. 3,876,716 and quaternary phosphonium compounds, such as those disclosed in U.S. Pat. No. 3,639,493.

Other optional components may be present in the reaction mixture, for example inhibitors, stabilizers and dispersants. The use of such optional components will depend on the nature of the reactants and products to be produced.

In the process of the present invention the composition comprising 1,2,3,4-tetrachlorobutane and the base is contacted in a reactor in a liquid phase, thereby initiating an exothermic reaction resulting in the attainment of a temperature sufficient to dehydrochlorinate the 1,2,3,4-tetrachlorobutane to produce a dehydrochlorinated product. It is preferred that the reactor is a multi-stage bubble reactor, but other reactors such as continuous tank or single stage boiling reactors may be used. Bubble reactors are preferred because in such reactors the heat liberated during the reaction vaporizes the product, i.e. the dehydrochlorinated compound thus produced and this vapor provides a means for agitation.

A preferred process for dehydrohalogenation of chlorinated alkenes is described in detail in U.S. Pat. No. 6,380,446. The reactor described is a multi-stage type, preferably having at least three stages, most preferably 4-20 stages. Preferably the reactor will be a vertical column reactor because it greatly simplifies establishment of a cocurrent flow pattern. Such a flow pattern is conducive to attainment of high conversion. That is, when a cocurrent upflow reactor is employed, vaporized product will rise along with reactants due to its buoyancy. Agitation caused by the movement of gaseous product through the liquid phase eliminates the need for mechanical agitators. In other embodiments, the dehydrohalogenation process step of the present invention can take place in a series of continuous, distinct tanks or vessels.

In a preferred embodiment, the composition comprising 1,2,3,4-tetrachlorobutane and aqueous alkali metal hydroxide will be pre-mixed before introduction to the reactor. Examples of mixing devices include tanks fitted with mechanical agitators, stirred tank reactors, continuous stirred tank reactors, pumps and motionless stationary mixers. Reaction is initiated in the mixing device. This exothermic reaction provides heat and raises the vapor pressure to the point where some evaporation occurs upon entry to the bubble reactor. Some evaporation may also occur in the first mixing device, especially if it is a stirred reactor. Mixing devices that are particularly useful in the practice of the invention include homogenizers, colloid mills, stirred tank reactors and centrifugal pumps.

The dehydrochlorination reaction produces 2,3-dichlorobutadiene-1,3 and various isomeric butenes, such as 1,2,4-trichloro-2-butene; 2,3,4-trichloro-1-butene, other dichlorobutadiene isomers such as both e and z isomers of both 1,2 and 1,3-dichlorobutadiene-1,3 and other chlorinated byproducts, such as chlorinated alcohols. One isomer, 2,3,4-trichlorobutene-1, will undergo dehydrochlorination to produce 2,3-dichlorobutadiene-1,3. The 2,3-dichlorobutadiene-1,3 and many of the chlorinated byproducts have boiling points lower than that of 1,2,3,4-tetrachlorobutane. Thus, if isolation of 2,3-dichlorobutadiene-1,3 by distillation were conducted at this stage, a mixture of 2,3-dichlorobutadiene-1,3 and both e and z isomers of both 1,2 and 1,3-dichlorobutadiene-1,3 would be obtained.

The dehydrochlorination reaction produces a mixture that has at least two phases, an aqueous phase and an organic phase comprising the mixture of 2,3-dichlorobutadiene-1,3 and chlorinated byproducts. The chlorinated byproduct composition may contain chlorinated butenes and other chlorinated compounds as well as the dichlorobutadiene-1,3 isomers having at least one alpha-chlorine substituent. When the dehydrochlorination reaction is conducted in a bubble reactor a mixture comprising 2,3-dichlorobutadiene 1,3; chlorinated byproducts; unreacted 1,2,3,4-tetrachlorobutane; intermediates; and water is formed in the initial dehydrochlorination step and this mixture is vaporized to form a single vapor phase, which when condensed forms an aqueous phase and an organic phase.

In order to purify and isolate the 2,3-dichlorobutadiene-1,3 that is the desired product of the dehydrochlorination reaction, the phase containing the mixture of 2,3-dichlorobutadiene-1,3 and chlorinated byproduct composition is usually and preferably separated from the aqueous phase and further treated. The separation may be conducted by any means, but may be preferably carried out by distillation or steam stripping followed by decantation or centrifugation. When a bubble reactor is utilized, the phase containing the mixture of 2,3-dichlorobutadiene-1,3 and byproduct composition is vaporized, along with water. A vapor phase containing 2,3-dichlorobutadiene-1,3, byproduct, unconverted reactants and intermediates, and water is condensed overhead, The organic phase containing 2,3-dichlorobutadiene-1,3 may be separated by decantation or centrifugation.

Once separated from the aqueous phase, the phase containing the 2,3-dichlorobutadiene-1,3 is contacted with gaseous chlorine, preferably in the presence of an ionic catalyst. Alternatively, the first reaction product, containing both the aqueous phase and organic phase may be contacted with gaseous chlorine, without separation of the phases. The former method wherein the phases are separated is preferred because yields are higher and subsequent product isolation is less problematic.

The ionic catalysts useful in the chlorination step are chloride ion sources that may be added to the reaction mixture in the form of chloride salts or in the form of materials that will react with a component of the reaction mixture to produce a chloride salt in situ, i.e. a catalyst precursor. Representative examples of suitable compounds which act as ionic catalysts for the reaction are quaternary ammonium chlorides, quaternary phosphonium chlorides and ternary sulfonium chlorides. Hydrochlorides of primary, secondary, or tertiary amines can also be utilized. Examples of materials which may be added to form the catalyst in situ include amines, either primary, secondary, or tertiary, or the analogous phosphines or sulfides. These compounds are capable of reacting with one or more of the chlorine-substituted materials in the reaction mixture or with hydrogen chloride to form a chloride ion source. Other examples of precursors for chloride ions are salts in which the anion is not a chloride ion but which can undergo an ion exchange reaction in the reaction medium to produce a chloride ion. Quaternary ammonium chlorides are a preferred catalyst type because they are widely available commercially as surface active agents. Representative quaternary ammonium compounds include butyltriethylammonium chloride, dilauryldimethylammonium chloride, amyltriethylammonium chloride, tetraoctylammonium chloride, hexyltrimethylammonium chloride and the like. Suitable quaternary phosphonium compounds include, for example, tetrabutylphosphonium chloride, methyltrioctylphosphonium chloride, trimethyloctadecenylphosphonium chloride, and triethyl-(2-bromoethyl)phosphonium chloride. Sulfonium compounds that may be used as catalysts include trimethylsulfonium chloride, dihexylethylsulfonium chloride, dihexylethylsulfonium chloride, methyldioctadecylsulfonium chloride, dibutylpropylsulfonium chloride and cyclohexyldimethylsulfonium chloride. It is usually more convenient to form the catalyst in situ, for example by adding an amine as a free base which can then react to form the chloride ion source in the reaction mixture. Pyridine is particularly useful as a catalyst precursor. Other compounds which will form catalysts in situ in the reaction medium are the carboxylic acid amides such as formamide, acetamide, 2-pyrrolidone, 2-piperidone, and N-butylacetamide. Other useful catalyst precursors include 1,8-diazabicyclo[5.4.0]undec-7-ene-1,8 and N-methylpyrrolidone. The catalyst precursor concentration generally ranges from 20-200 ppm based on the amount of liquid in the reaction mixture. However, as much as 1% may be used, depending on the particular catalyst.

The process is preferably, although not necessarily, carried out in the presence of free radical inhibitors. Conventional free radical inhibitors include oxygen, phenols such as 4-tert-butyl catechol, aromatic amines, such as phenyl alpha-naphthylamine, phenothiazine, and N'-nitrosodiphenylamine, and other inhibitors, such as sulfur. Practical inhibitor concentrations have been found to be about 20-80 ppm based on the amount of liquid present in the reaction mixture.

Preferably, the chlorine will have a purity of at least 90%, more preferably 96%. The conditions used during the chlorination are such that no more than 20% of the 2,3-dichlorobutadiene-1,3 present in the composition that is to be contacted with chlorine is further chlorinated.

It has been found that if chlorine of lower purity is used, yield is reduced, for example by up to 5%. In addition, the presence of inert contaminants that are sometimes present in commercial sources of chlorine, for example carbon dioxide, hydrogen chloride and nitrogen, may present environmental hazards necessitating additional treatment equipment and processes, thereby adding cost and complexity.

The chlorination reaction may take place in any of a variety of reactors. For example, plug flow, continuous stirred tank, bubble column, loop, and batch reactors may be employed. Plug flow and batch reactors are preferred. Continuous stirred tank reactors are not favored because yield is compromised. This is because chlorination of the desired isomeric product that contains beta-chlorine substituents exclusively is increased in these types of reactors. With sufficient catalyst the reaction is extremely rapid and formation of high temperature hot spots may require the use of jacketed plug flow reactors to control the hot spot temperature. Process dwell time at the hot spot location should be minimized and temperatures above 125° C. should be limited to a few seconds to minimize dimerization of the 2,3-dichlorobutadiene-1,3 monomer. It is advantageous when using a jacketed plug flow reactor to have a dwell time long enough to permit cooling of the process liquid to sub-ambient, for example subzero, temperatures after chlorination reaction takes place. Generally the chlorination reaction will take place at temperatures of between 0° C. and 150° C.

The chlorinated butenes that are present in the chlorinated byproduct of the dehydrochlorination reaction are more reactive toward chlorine than is 2,3-dichlorobutadiene-1,3. Chlorination of the mixture of chlorinated butenes and 2,3-dichlorobutadiene-1,3 consequently results in the production of a reaction product that is a mixture of 2,3-dichlorobutadiene-1,3 and a highly chlorinated byproduct composition. The resultant highly chlorinated byproduct composition is made up of species that have considerably higher boiling points than 2,3-dichlorobutadiene-1,3. The unusual magnitude of the reactivity difference with respect to chlorination of 2,3-dichlorobutadiene-1,3 versus the byproduct chlorinated butene isomers and other chlorinated species is unexpected. Although it is believed that the source of this reactivity difference is the difference in chemical structure related to the presence of alpha-chlorine substituents versus beta-chlorine substituents, the magnitude exceeds that which would normally be anticipated. Because of this unexpected difference it is possible to conduct the chlorination reaction under conditions wherein the chlorinated byproduct of the dehydrochlorination reaction is preferentially chlorinated compared to the 2,3-dichlorobutadiene-1,3. In fact, it is possible to conduct the chlorination reaction under conditions such that the byproduct composition is further chlorinated but further chlorination of the 2,3-dichlorobutadiene-1,3 that is present is limited to less than 20%. Preferably, less than 10% of the 2,3-dichlorobutadiene-1,3 that is present will be further chlorinated and more preferably less than 5% of the 2,3-dichlorobutadiene-1,3 that is present will be chlorinated.

Typical conditions for obtaining such results include reaction of the composition comprising 2,3-dichlorobutadiene-1,3 and chlorinated byproduct in the above-described reactors with an amount of chlorine that is between 0.5 and 3.0 moles of chlorine per mole of chlorinated butenes having alpha-chlorine substituents that are present in the composition. Preferably between 0.75 and 2.5 moles of chlorine per mole of chlorinated butenes having alpha-chlorine substituents will be used and most preferably between 0.85 and 2.25 moles of chlorine per mole of chlorinated butenes having alpha-chlorine substituents will be used.

Because of the highly chlorinated nature of the chlorinated byproduct composition the reaction product is easily and economically separated into a relatively pure 2,3-dichlorobutadiene-1,3 fraction and a concentrated highly chlorinated byproduct. Separation (i.e. isolation) may be accomplished for example by flashing off the fraction containing the lower boiling 2,3-dichlorobutadiene-1,3 or by freezing out the byproduct. Flashing off the lower boiling fraction is preferred. The boiling points of the 2,3-dichlorobutadiene-1,3 and most of the highly chlorinated byproducts will differ to such a degree that complex distillation columns are not necessary and high purity product, i.e. having a purity of 90% or greater, can be achieved with less than 4 theoretical fractionation stages.

The process of the present invention provides an efficient means for obtaining 2,3-dichlorobutadiene-1,3 composition from 1,2,3,4-tetrachlorobutane which composition is relatively free of dichlorobutadienes containing chlorine at an alpha carbon. It has not been possible using prior art methods to produce 2,3-dichlorobutadiene-1,3 from 1,2,3,4-tetrachlorobutane in a manner in which separation from the chlorinated byproduct composition is as efficient and economical as in the present process. It has also not been possible using prior art methods to produce 2,3-dichlorobutadiene-1,3 from 1,2,3,4-tetrachlorobutane in a manner that results in production of a product that contains only one significant isomer byproduct that contains alpha chlorine substituents rather than two, three or four isomeric byproducts that contain alpha-chlorine substituents.

The invention is further illustrated by the following examples of certain embodiments.

EXAMPLES

Example 1

A reactor equipped with an air-driven agitator was charged with 100 parts by mole of meso-1,2,3,4-tetrachlorobutane, bis(beta-hydroxypropyl)coco-benzylamine chloride phase transfer catalyst and an aqueous mixture of phenothiazine in water. The amount of phase transfer catalyst in the mixture was 1 wt % based on the total organic feed and the amount of phenothiazine in the mixture was 2000 parts per million by wt. based on the total organic feed. The temperature of the mixture was adjusted to 80° C. and then 220 parts by mole of sodium hydroxide in an aqueous solution (18 wt. % sodium hydroxide) was added to the organic mixture over a period of approximately 10 minutes. The temperature of the reactor was controlled between 60° C. and 80° C. by evaporative removal of product. Vapor was removed overhead and condensed until the reaction stopped, approximately 30 minutes from the time the addition of sodium hydroxide solution was initiated. The overhead condensate liquid was decanted to separate an organic liquid phase from an aqueous phase. The organic phase contained 72.4 mole % 2,3-dichlorobutadiene-1,3, 2.5 mole % 1,2,4-trichloro-2-butene, 0.9 mole % 2,3,4-trichlorobutene-1, 1.0 mole % unreacted meso-tetrachlorobutane, 20.9 mole % other dichlorobutadiene isomers and 2.3 mole % of unidentified compounds.

The organic phase was introduced to a stirred reactor and 1 wt. % N-methylpyrrolidone was added. Chlorine vapor from a high purity chlorine lecture bottle (99.9% pure) at ambient temperature was bubbled through the liquid and aliquots were removed at intervals to monitor composition. The chlorine flow was continued until only two dichlorobutadiene isomers were detectable by gas chromatographic analysis. The mixture was then heated to 60° C. and evaporated until the level of dichlorobutadiene isomers in the heel had diminished to below 10% as determined by gas chromatographic analysis. The overhead vapor was condensed. The condensed product contained 95% 2,3-dichloro-1,3-butadiene and 5% of another dichlorobutadiene isomer.

What is claimed is:

1. A process for production of a composition comprising 2,3-dichlorobutadiene-1,3, the process comprising the steps of:
   A. contacting a composition comprising 1,2,3,4-tetrachlorobutane with an aqueous mixture comprising a base having a $K_b$ of at least $10^{-9}$, at a temperature sufficient to dehydrochlorinate the 1,2,3,4-tetrachlorobutane, thereby forming a first reaction product having at least two phases, 1) a first phase comprising a mixture of a) 2,3-dichlorobutadiene-1,3 and b) a chlorinated byproduct comprising chlorinated butenes other than 2,3-dichlorobutadiene-1,3 and 2) a second phase comprising an aqueous phase;
   B. separating said first phase from said aqueous phase;
   C. contacting said first phase, after it has been separated from said aqueous phase, with chlorine having a purity of at least 96% in an amount sufficient to further chlorinate said chlorinated byproduct but insufficient to cause conversion of more than 20% of the 2,3-dichlorobutadiene-1,3 present in said first phase to more highly chlorinated species, thereby producing a second reaction product; and
   D. isolating from said second reaction product a composition comprising 2,3-dichlorobutadiene-1,3 wherein at least 90 weight percent of said composition is 2,3-dichlorobutadiene-1,3, based on the total weight of said composition.

2. A process of claim 1 wherein step A is conducted in the presence of a phase transfer catalyst.

3. A process of claim 1 wherein step C is conducted in the presence of an ionic catalyst.

4. A process of claim 1 wherein step A is conducted in a bubble reactor.

5. A process of claim 4 wherein a mixture comprising 2,3-dichlorobutadiene 1,3; chlorinated byproducts; unreacted 1,2,3,4-tetrachlorobutane; intermediates; and water is formed in step A and said mixture is vaporized to form a single vapor phase, which vapor phase, when condensed, forms an aqueous phase and an organic phase.

6. A process for production of a composition comprising 2,3-dichlorobutadiene-1,3, the process comprising the steps of:
   A. contacting a composition comprising 1,2,3,4-tetrachlorobutane with an aqueous mixture comprising a base having a $K_b$ of at least $10^{-9}$ at a temperature sufficient to dehydrochlorinate the 1,2,3,4-tetrachlorobutane, thereby forming a first reaction product having at least two phases, 1) a first phase comprising a mixture of a) 2,3-dichlorobutadiene-1,3 and b) a chlorinated byproduct comprising chlorinated butenes other than 2,3-dichlorobutadiene-1,3 and 2) a second phase comprising an aqueous phase;
   B. contacting said first reaction product with chlorine of at least 96% purity in an amount sufficient to further chlorinate said chlorinated byproduct but insufficient to cause conversion of more than 20% of the 2,3-dichlorobutadiene-1,3 present in said first phase to more highly chlorinated species, thereby producing a second reaction product; and
   C. isolating from said second reaction product a composition comprising 2,3-dichlorobutadiene-1,3 wherein at least 90 weight percent of said composition is 2,3-dichlorobutadiene-1,3, based on the total weight of said composition.

* * * * *